United States Patent [19]

Larkin

[11] E Patent Number: Re. 32,935

[45] Reissued Date of Patent: May 30, 1989

[54] NON-TOXIC ORGANOTIN STABILIZERS FOR VINYL CHLORIDE POLYMERS

[75] Inventor: William A. Larkin, Avon-by-the-Sea, N.J.

[73] Assignee: M&T Chemicals, Inc., Rahway, N.J.

[21] Appl. No.: 798,637

[22] Filed: Nov. 15, 1985

Related U.S. Patent Documents

Reissue of:

[64] Patent No.: 4,496,490
Issued: Jan. 29, 1985
Appl. No.: 120,753
Filed: Feb. 12, 1980

U.S. Applications:

[60] Continuation-in-part of Ser. No. 43,997, May 31, 1979, abandoned, which is a continuation of Ser. No. 454,363, Mar. 25, 1974, abandoned, which is a division of Ser. No. 343,648, Mar. 22, 1973, abandoned.

[51] Int. Cl.[4] ..... B65D 85/00; C07F 7/22

[52] U.S. Cl. ..... 426/106; 426/131; 426/415; 556/93; 556/96; 556/97; 556/102

[58] Field of Search ..... 556/93, 96, 97, 102; 426/106, 131, 415

[56] References Cited

U.S. PATENT DOCUMENTS 3,657,294 4/1972 Glaskey ..... 556/88 X

FOREIGN PATENT DOCUMENTS 869588 4/1971 Canada .
6896 2/1972 Japan .
7639 4/1972 Japan .
39570 10/1972 Japan .
1326057 8/1973 United Kingdom .
1349913 10/1974 United Kingdom .

OTHER PUBLICATIONS

Arch. Toxikol 26 196–202 (1970).
Plaste & Kantschuk 19, (5), pp. 325–336 (1972).
Fortschritte der Chemischen Forschung 16 (3/4), pp. 393–403 (1971).
Neumann, The Organic Chemistry of Tin, John Wiley & Sons, Intersc. Publ., N.Y., pp. 230–237; 240–242 (1970).
Bokranz et al, Fortschritte der Chemischen Forschung, vol. 16, Nos. 3–4, pp. 365 and 398–404 (1971).

*Primary Examiner*—Curtis R. Davis
*Attorney, Agent, or Firm*—Burns, Doane, Swecker & Mathis

[57] ABSTRACT

Vinyl chloride polymers suitable for use in food packaging materials are stabilized against discoloration and embrittlement resulting from exposure to heat using mono-n-octyltin compounds of the general formula $H_{17}C_8Sn(SCH_2COOR')_3$, wherein R′ represents an alkyl radical containing eight carbon atoms.

17 Claims, No Drawings

NON-TOXIC ORGANOTIN STABILIZERS FOR VINYL CHLORIDE POLYMERS

Matter enclosed in heavy brackets [ ] appears in the original patent but forms no part of this reissue specification; matter printed in italics indicates the additions made by reissue.

BACKGROUND OF THE INVENTION

This application is a continuation-in-part of Application Ser. No. 043,997, filed May 31, 1979, now abandoned, which in turn is a continuation of Application Ser. No. 454,363, filed Mar. 25, 1974, now abandoned, which in turn is a divisional of Application Ser. No. 343,648, filed Mar. 22, 1973, now abandoned.

The present invention concerns non-toxic organotin stabilizers. More particularly, this invention relates to liquid organotin stabilizer compositions that are sufficiently low in toxicity to be suitable for use with halogen-containing polymers that are employed as food packaging and handling materials and beverage containers.

Polyvinyl chloride and other halogen-containing polymers are inherently unstable when exposed to temperatures above about 100° C. for the extended periods of time required for melt processing and shaping. A variety of compounds effectively prevent or delay the discoloration and embrittlement exhibited by vinyl chloride polymers at these temperatures. The increasing use of vinyl chloride polymers as food packaging materials in the form of films, bottles, pipes, trays and other containers has been made possible by the development of stabilizers which inhibit heat-induced discoloration and decomposition of the polymer, yet are of sufficiently low toxicity for use in materials that are in contact with food and beverages.

Organotin compounds have long been recognized as one of the most effective stabilizers for vinyl chloride homopolymers and copolymers. U.S. Pat. No. 2,789,963 discloses a variety of organotin compounds that are suitable for this purpose. Diorganotin dimercaptides and bis(mercaptocarboxylic acid esters) are particularly preferred classes of stabilizers. A shortcoming of many of these organotin compounds, which can be represented by the general formulae $R_2Sn(SR')_2$ and

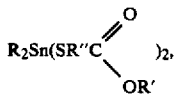

wherein R and R' represent monovalent hydrocarbon radicals and R'' represents a divalent hydrocarbon radical, is that they are too toxic for use in food packaging materials. It has been reported by Katsumura et al. in U.S. Pat. No. 3,390,159 that di-n-octyltin derivatives are considerably less toxic than other organotin stabilizers for polyvinyl chloride. At present only one member of this class of compounds, di-n-octyltin-S,S'-bis(isooctyl mercaptoacetate) has been approved by the United States Food and Drug Administration for use as a stabilizer in food packaging materials. The aforementioned U.S. Pat. No. 3,390,159 is concerned with a process for preparing di-n-octyltin oxide from the corresponding di-n-octyltin dichloride in the absence of impurities. These impurities result from the presence in the crude di-n-octyltin dichloride of significant amounts of n-octyltin trichloride and tri-n-octyltin chloride. The inorganic tin compounds that may also be present include stannic chloride and stannous chloride. Both of these compounds exhibit relatively little, if any, toxicity. The organotin compounds which are often present as impurities allegedly increase the toxicity of the resultant di-n-octyltin oxide, which is subsequently employed as a starting material for the preparation of low toxicity stabilizers for vinyl chloride polymers. U.S. Pat. No. 3,640,947, issued to C. R. Gloskey, discloses that a mixture of octyltin oxides employed to prepare a non-toxic octyltin stabilizer composition contains not more than 5% by wieght of mono-n-octylstannoic acid, the precursor of n-octyltin-S,S',S''-tris(isooctyl mercaptoacetate). The final stabilizer is obtained by reacting the mixture of n-octyltin oxides with isooctyl mercaptoacetate. Had either Katsumura et al. or Gloskey recognized that mono-n-octyltin-S,S',S''-tris (isooctyl mercaptoacetate) was equally low in toxicity as the corresponding di-n-octyltin compound there would be no reason to limit the concentration of the mono-n-octyltin compound.

Available data concerning the relative toxicities of mono-, di- and trialkyltin compounds containing the same alkyl group are contradictory. For example, W. P. Neumann, in a text entitled "The Organic Chemistry of Tin" discloses that "(f) or the same alkyl group, maximum toxicity is found in the compound of type $R_3SnX$, followed by $R_2SnX_2$ and $R_4Sn$. $RSnX_3$ is the least toxic or non-toxic". In the same chapter Neumann presents a table of acute toxicity values determined by force-feeding relatively large amounts of the test chemical to rats. The lethal dose for ½ the population, referred to as $LD_{50}$, is greater than 6,000 mg per kilogram of body weight for tri-n-octyltin laurate and bis(tri-n-octyltin) sulfate. By comparison, the $LD_{50}$ values for the di-n-octyltin compounds reported ranges from 1975 for di-n-octyltin-S,S'-bis(isooctyl thioglycollate), referred to as di-n-octyltin-S,S'-bis(isooctyl mercaptoacetate) in the aforementioned Gloskey patent, to 4,500 for di-n-octyltin maleate. It is evident from these data that the diooctyltin compounds are from 1.3 to 3 times more toxic than two tri ooctylin compounds. The toxicity data reported by Neumann are not the result of work performed by the author, but rather the data are collected from articles by recognized toxicologists, including O. R. Klimmer. The relative toxicity data discussed in the preceding section of this paragraph are taken from a lecture given by Professor Klimmer at the Organotin Symposium at Frankfurt during November of 1963. Klimmer and J. G. A. Luijter, a recognized expert on the subject of organotin chemistry, are coauthors of a paper that was presented at a conference in Dusseldorf on Nov. 15, 1973. The conference was sponsored by the Tin Information Bureau, GmbH. In their paper Klimmer and Luitjen report that the acute oral toxicity of monooctyltin trichloride is greater than the toxicity of either dioctyltin dichloride or trioctyltin chloride. These data, when considered in combination with the aforementioned U.S. Pat. No. 3,640,947, which limits the combined maximum concentrations of the corresponding mono- and tri-n-octyltin compounds in a di-n-octyltin oxide composition employed to prepare a non-toxic stabilizer to 5% by weight of the di-n-octyltin compound, indicate that n-octyltin-S,S',S''-tris(isooctyl mercaptoacetate) would be more toxic than the stabilizer composition of the Gloskey patent. This is contrary to the aforementioned general statement by Neumann concerning the relative toxicities of mono-, di- and trialkyltin compounds.

Actute toxicity values are determined by force-feeding relatively large doses of the test compound to a group of rats or other animals and determining the concentration level which is lethal to a certain percentage of the population. While these data may be useful for certain applications of organotin compounds, they are insufficient to ascertain whether a given organotin compound is sufficiently low in toxicity for use in materials which come in contact with food. Various national health authorities, including the United States Food and Drug Administration, have established regulations concerning the type of toxicity data required to obtain registration for a material as a stabilizer for use in food packaging materials. These regulations require that an applicant submit sufficient data from long-term feeding studies on a variety of different animals, including dogs, to demonstrate that the health of these animals is not impaired and no observable damage to their internal organs is observed following daily consumption of given amounts of the test compound over a period of from 90 days to two years. It is impossible to determine if a given compound is sufficiently low in toxicity to allow its use in contact applications from the $LD_{50}$ value alone. Some compounds with very high $LD_{50}$ values fail totally in chronic feeding studies. A final determination cannot be made in the absence of the chronic toxicity data required by national health authorities such as the Food and Drug Administration. The need for these type of data is discussed in an article by P. Klimsch entitled "Recent Developments in the Stabilization of PVC" that appeared in Plaste und Kautschuk (Volume 19, No. 5, pages 325–43 and 360; 1972).

The criteria for determining whether a given ingredient in a plastic material constitutes a toxicity hazard has been defined by the United States Food and Drug Administration. These criteria are set forth in a comprehensive article that appeared in the October, 1955 issue of the Food Drug Cosmetic Law Journal. The criteria can be summarized as follows:

(1) An ingredient of a plastics material which is not extracted by a foodstuff with which it is in contact does not constitute a hazard.

(2) If a material is found in a food as a result of contact with a plastic, that material may constitute a toxic hazard if it is toxic in the biological sense, i.e. if it causes either an acute or chronic injurious effect by oral ingestion, inhalation, or absorption through the skin, in animals or humans. If no such effect can be shown the material does not constitute a hazard.

(3) Acute toxic levels are unlikely ever to be realised in practice. It is however possible that injurious effects may be produced by repeated small doses of a material extracted from a plastics and therefore it is chronic toxicity which should be used for the purpose of assessing the hazard.

(4) The toxic hazard of an ingredient of a plastics material is a function both of its chronic toxicity and of its extractability from plastics material under service conditions.

(5) For the purpose of assessment of the hazard, extractability tests must be carried out using the foodstuffs themselves or a range of representative extractants under conditions which simulate the most severe likely to be encountered in practice. The results of these tests must then be combined with the data on the chronic toxicities of the ingredients of the plastics as expressed by their Toxicity Factors to give the Toxicity Quotient, which is the measure of the hazard.

It should be evident from this discussion that the general statement "octyltin compounds are lower in toxicity than the corresponding lower alkyltin compounds" cannot be taken as an assurance that any octyltin compound is a potential food grade stabilizer in the absence of chronic toxicity and extractability data.

The only prior art references disclosing monooctyltin compounds mention these compounds and the corresponding triorganotin compounds only as undesireable contaminants produced during manufacture of the desired dioctyltin compound (the oxide in the case of the aforementioned Katsumura patent and the isooctyl mercaptoacetate in the Gloskey patent).

Katsumura nowhere discloses that any of the "n-octyltin compounds" are sufficiently low in toxicity to be employed as food grade stabilizers. The aim of the process claimed in the Katsumura patent is to reduce the concentration of the corresponding mono- and tri-n-octyltin compounds to virtually zero while Gloskey sets a limit of 5% by weight, based on di-n-octyl compound, for the combined concentration of mono- and tri-n-octyltin isooctyl mercaptoacetates.

As previously disclosed in this specification, the acute toxicity of mono-n-octyltin trichloride is significantly more severe than the corresponding di- or tri-n-octyltin chlorides. This is contrary to the generally accepted, although inaccurate, generalization that a monoalkyltin compound is less toxic than the corresponding di- and trialkyltin compounds. It has now been found that when the n-octyltin chlorides are converted to the corresponding isooctylmercaptoacetate derivatives, the relative order of acute toxicities is reversed, and the mono-n-octyltin compound is the least toxic. In addition, the results of long term feeding studies required by the United States Food and Drug Administration haven confirmed that the "no effect" level of mono-n-octyltin-S,S',S''-tris(isooctyl mercaptoacetate) is sufficiently low for this compound to be employed as a stabilizer for halogen-containing polymers employed as food packaging and handling materials. This compound is actually less toxic than the corresponding di-n-octyltin compound claimed in the aforementioned patent to Gloskey. This finding directly contradicts data concerning the relative toxicities of mono-, di- and triorganotin compounds that were published prior to March, 1973, the filing date of Applicant's earliest application disclosing the present stabilizer compositions.

SUMMARY OF THE INVENTION

This invention provides a liquid food grade organotin stabilizer composition for polyvinyl chloride and copolymers of vinyl chloride with copolymerizable ethylenically unsaturated compounds, said composition consisting of at least one mono-n-octyltin compound corresponding to the general formula n-$C_8H_{17}Sn(SCH_2COOR')_3$, said composition containing between 0 and 5% by weight of other octyltin derivatives. R' in the foregoing formula represents an alkyl radical containing eight carbon atoms.

As used in this specification the term "food grade" defines a stabilizer composition which complies with the following criteria:

1. An acute oral toxicity ($LD_{50}$) of greater than 1 gram per kilogram of body weight.

2. A maximum extraction from polyvinyl chloride by foodstuffs of less than 1 part per million (ppm), and 3. A "no effect" level for dogs of 300 parts per million for each kilogram of food.

DETAILED DESCRIPTION OF THE INVENTION

The stabilizers of this invention contain between 95 and 100% by weight based on total organotin compounds, of at least one mono-n-octyltin derivative corresponding to the general formula set forth in the preceding section of this specification. The remaining organotin compounds are by-products formed during the preparation of the mono-n-octyltin derivative.

The present stabilizers are light yellow liquids at a temperature of 25° C., contain between 13 and 15% by weight of tin, and exhibit a density of about one gram per c.c. The apparent discrepancy between these limits for tin content and the requirement that at least 95% of the organotin compounds present in the stabilizer be monooctyltin-S,S',S''-tris(mercaptoacetic acid esters) is due to the presence in the stabilizer composition of relatively small amounts of unreacted starting materials and solvents employed in the preparation of the present stabilizers. Even with extensive purification it is extremely difficult if not impossible to remove the last traces of these materials, none of which are present in amounts sufficient to increase the toxicity of the present stabilizers to any significant extent.

The mono-n-octyltin mercaptoacid ester stabilizers of this invention are conveniently prepared by reaction of an n-octyltin trihalide with a mercaptoacetic acid ester of the general formula

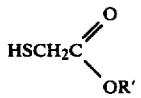

wherein R' represents an alkyl radical containing eight carbon atoms. Iso-octylmercaptoacetate, 2-ethylhexylmercaptoacetate and n-octylmercaptoacetate are the preferred esters. The preferred n-octyltin trihalide is the chloride, which is usually less expensive and more readily available than the corresponding bromide or iodide.

The reaction between the mercaptoacetic acid ester and an n-octyltin trihalide can be conducted at temperatures between ambient and 100° C. A liquid hydrocarbon provides a suitable reaction medium, a preferred hydrocarbon being cyclohexane. A water-soluble base such as ammonia or an alkali metal hydroxide is usually employed to neutralize the hydrogen halide formed as a by-product of the reaction. The resultant salt is insoluble in the organic phase of the reaction medium, thereby displacing the equilibrium of the reaction toward formation of the desired mono-n-octyltin mercaptoacid ester. The reaction is preferably conducted by gradually adding an aqueous solution of the base to a mixture of the n-octyltin trihalide, mercaptoacid ester and liquid hydrocarbon. The n-octyltin mercaptoacid ester product is isolated from the organic portion of the resultant two-phase reaction mixture.

To maximize product yield, it may be desirable that the isooctylmercaptoacetate be present in slight excess over the 3:1 molar ratio required by the stoichiometry of the reaction as represented by the equation

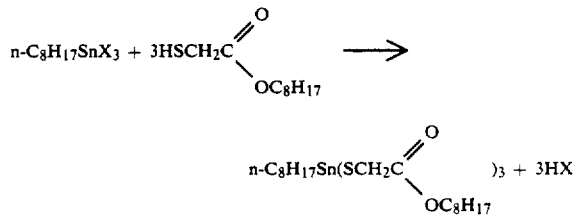

wherein X represents chlorine, bromine or iodine. The n-octyltin trihalide is conveniently prepared by a disproportionation type reaction between a stannic halide, preferably the chloride, and tetra-n-octyltin, the latter being the major product obtained from the reaction of an n-octylmagnesium halide with a stannic halide in a molar ratio of 4:1. The conditions for the latter reaction are extensively described in the chemical literature, for example in U.S. Pat. No. 2,675,398. The disproportionation reaction between a tetraorganotin compound and a stannic halide to yield a monoorganotin derivative is also disclosed, for example in British Pat. No. 739,883. In order to avoid extensive purification of the final product the n-octyltin trihalide should preferably contain less than 5% by weight of other organotins.

In an alternative method for preparing n-octyltin trihalides, tri-n-octyl aluminum is substituted for the n-octylmagnesium halide. The reaction between a stannic halide and n-octyl sodium can also be employed to prepare tetra-n-octyltin.

The low toxicity mono-n-octyltin S,S',S''-tris(mercaptoacetic acid ester) stabilizers of this invention are incorporated using conventional melt blending techniques into vinyl chloride polymers in amounts of between 0.1 and 5% by weight, preferably between 1 and 2%.

As used throughout this specification, the term "vinyl chloride polymers" is intended to include those polymers which can be stabilized against heat-induced discoloration and embrittlement using the present mono-n-octyltin compounds. Suitable polymers include homopolymers of vinyl chloride and copolymers containing vinyl chloride as the major component with other ethylenically unsaturated monomers. Useful comonomers include but are not limited to acrylic acid, methacrylic acid and esters of these acids derived from aliphatic alcohols containing 1 to 20 carbon atoms; other suitable comonomers are acrylonitrile, vinyl monomers such as styrene and vinyl esters of carboxylic acids, unsaturated acids including maleic acid, the anhydrides and esters of unsaturated acids and olefinic hydrocarbons such as ethylene and propylene. Suitable comonomers are selected on the basis of their relative reactivities with vinyl chloride as disclosed in the chemical literature, for example "The Polymer Handbook", edited by J. Brandrup and E. H. Immergut (Interscience Publishers, 1966).

The stabilized polymer compositions may also contain such additives as pasticizers and anti-oxidants. The preferred pasticizers, used in amounts of up to about 15% in semi-rigid formulations and 50 to 60% in film, are the non-toxic pasticizers such as butylbenzyl phthalate, dicyclohexyl phthalate, dihexyl phthalate, and di-2-ethylhexyl adipate. The resins used for preparing bottles may contain an impact modifying rubbery polymer, such acrylonitrile-butadiene-styrene, or polymers derived from esters of acrylic or methyacrylic acid in an amount between about 3 and 20%, based on the weight of the resin. The preferred antioxidants are the hindered phenols, particularly 2,6-di-tert-butyl-p-cresol, and are used in very small amounts, e.g., 0.1 to 0.2%, based on the weight of the resin being stabilized.

The present polymer compositions may incorporate non-toxic auxiliary stabilizers. Examples of suitable auxiliary stabilizers are the calcium, zinc and stannous salts of carboxylic acids, including the stearates and benzoates; organic phosphites, including tri(nonylphenyl) phosphite; and epoxidized oils, including soybean oil.

Di-n-octyltin-S,S'-bis(isooctylmercaptoacetate) is a preferred auxiliary stabilizer. It has been observed that mixtures containing up to about 75% by weight of this compound with mono-n-octyltin S,S',S''-tris(isooctylmercaptoacetate) impart unexpectedly high levels of heat stability to vinyl chloride polymers. Mixtures containing 73% of the mono- and 27% of the di-n-octyltin derivative are particularly preferred. Non-toxic lubricants, ultra-violet light absorbers, and dyes may also be present. Many of these modifiers and processing aids have been approved for use in food packaging materials.

The vinyl chloride polymer, stabilizer and any other desired additives are combined by milling, blending, or other commonly employed formulation technique which uniformly disperses all the additives, particularly the stabilizer, throughout the resin composition. Sheet or film products are commonly prepared on mills such as 2-roll differential speed mills, calenders and extruders. Semi-rigid products and rigid products can be formed using various casting techniques and by blow molding. Bottles can be produced by blow molding.

The advantages of the present invention are demonstrated by means of the following examples wherein all parts and percentages are by weight unless otherwise specified. The examples represent preferred embodiments of the invention and should therefore not be interpreted as limiting the scope thereof either with regard to stabilizing composition or suitable polymers.

EXAMPLE I

Preparation of n-octyltin-S,S',S'' tris(isooctylmercaptoacetate)

A reaction vessel was charged with 750 g. of n-octyltin trichloride (99.2% pure), 1387.5 g. of isooctylmercaptoacetate and 750 g. of cyclohexane. 450 g. of an aqueous solution containing 25% by weight of ammonia (calculated as ammonium hydroxide) was gradually added with agitation to the resultant mixture at a rate such that the temperature of the reaction mixture did not exceed 50° C. The contents of the reaction vessel were stirred for one hour following completion of the addition, after which 2,025 g. of water were added to dissolve the ammonium chloride formed during the reaction. Following the addition of 750 g. of cyclohexane the aqueous portion was separated from the resultant two-phase liquid and discarded. The organic portion was freed from the remaining water by azeotropic distillation under reduced pressure at a temperature of 110° C.

The n-octyltin trichloride employed as a starting material can be prepared using methods described in the prior art, for example in British Pat. No. 739,883, the disclosure of which is incorporated herein by reference.

The resultant almost colorless liquid product was found upon analysis to contain the following percentage by weight of elements:

tin—13.73%(theoretical=14.12%)

sulfur—11.23%(theoretical=11.42%)

Mono-n-octyltin-S,S',S''-tris(2-ethylhexylmercaptoacetate) can be prepared using the reaction conditions described in this example and substituting an equal weight of 2-ethylhexyl mercaptoacetate for the corresponding isooctyl ester.

EXAMPLE II

This example demonstrates the low degree of extractability from polyvinyl chloride that characterizes the present stabililizers.

A mixture containing 100 parts of a commercially available vinyl chloride homopolymer(Solvic 223), 0.02 part of a half glycol ester -half calcium soap of montanic acid (available as Hoechst Wax OP) together with 1.5 parts of mono-n-octyltin-S,S',S''-tris(isooctylmercaptoacetate) was blended by placing the components on a 2-roll mill wherein the roll temperature was between 160° and 170° C. During the three minute milling period a continuous sheet formed around one of the rollers and was removed. The sheet measured 1.3 m.m. in thickness and about 300 cm.$^2$ in area. The sheet was pressed at a temperature of 170° C. to obtain a thickness of 1.2 m.m. The total pressing time, including a two minute preheating period, was five minutes. Square samples measurng 30 cm.$^2$ in total surface area were immersed in one of the extractants for 10 days, during which time the temperature of the extractant was maintained at 40° C. The extractants employed were distilled water, a 3% aqueous solution of acetic acid, peanut oil and a 10% by weight aqueous solution of ethanol. With the exception of the peanut oil, a 300 c.c. portion of the extractant was employed for the test. The quantity of peanut oil was 30 c.c.

The migration of stabilizer from the polyvinyl chloride sample into the extractant was determined by measuring the concentration of tin in the extractant using colormetric analysis of the tin - pyrocatechol violet complex. The method is described by Newman and Jones [Analyst 91 (1966) 406–410]. In no instance did the amount of stabilizer extracted exceed 0.05 mg. per square decimeter of sample surface area.

A number of 16 ounce (475 cc) capacity cylindrical bottles were prepared by blow molding using the following formulation:

| | Parts (by weight) |
|---|---|
| Vinyl chloride homopolymer | 100.0 |
| Acrylic polymer processing aid (K-120N) | 3.0 |
| Acrylic polymer impact modifier (KM-611) | 12.0 |
| Carboxylic ester wax (Wax E) | 1.0 |
| Alizarin dye | 0.0004 |
| Stabilizer | 3.0 |

The three stabilizers evaluated were n-octyltin-S,S',S''-tri(isooctyl mercaptoacetate), di-n-octyltin-S,S'-bis(isooctyl mercaptoacetate) and a mixture containing equal parts by weight of these two compounds.

The bottles were filled with the desired extractant and then placed in an oven maintained at a temperature of 49° C. for the time periods specified in the following table. A portion of the contents of the bottle was then analyzed to determine the concentration of tin.

| Extraction Medium | Residence Time @49° C. (hours) | Tin Content (ppm) A | B | C |
|---|---|---|---|---|
| Distilled Water | 72 | 0.00 | 0.00 | 0.00 |
| | 96 | 0.00 | 0.00 | 0.00 |
| | 120 | 0.00 | 0.00 | 0.00 |
| 3% Acetic Acid* | 24 | 0.02 | 0.00 | 0.01 |
| | 48 | 0.03 | 0.00 | 0.01 |
| | 72 | 0.02 | 0.00 | 0.01 |
| 8% Ethanol* | 24 | 0.00 | 0.00 | 0.00 |
| 50% Ethanol | 24 | 0.01 | 0.03 | 0.02 |
| | 48 | 0.02 | 0.05 | 0.02 |
| | 72 | 0.02 | 0.03 | 0.02 |
| Heptane | 6 | 0.02 | 0.03 | 0.03 |
| | 8 | 0.03 | 0.02 | 0.03 |
| | 10 | 0.03 | 0.02 | 0.03 |

*In an aqueous solution
A-mono-n-octyltin-S,S',S''—tris(isooctyl mercaptoacetate)
B-di-n-octyltin-S,S'—bis(isooctyl mercaptoacetate)
C-1:1 (by weight) ratio mixture of A + B

EXAMPLE III

This example demonstrates the low acute toxicity of mono-n-octyltin-S,S',S''-tris(isooctylmercaptoacetate).

Young albino rats were used as the test animals. All animals were kept under observation for five days prior to experimental use, during which period they were checked for general physical health and suitability as test animals. The animals were housed in stock cages and were permitted a standard laboratory diet plus water ad libitum, except during the 16-hour period immediately prior to oral intubation, when food was withheld.

Selected groups of four male albino rats each were administered the undiluted test material at dose levels of 900, 1350, 2,025 and 3,038 mg. per kilogram of body weight. All doses were administered directly into the stomachs of the rats using a hypodermic syringe equipped with a ball-tipped intubating needle.

After oral administration of the test material, the rats were housed individually in suspended, wire-mesh cages and observed for the following 14 days. A necropsy was conducted on any animal which died during the study and on all animals sacrificed at the end of the 14-day observation period.

The acute oral median lethal dose ($LD_{50}$) was calculated using the techniques of Weil, Thompson and Thompson and Weil as reported in the following references:

Weil, Carrol S.: Tables for Convenient Calculation of Median-Effective Dose($LD_{50}$ or $ED_{50}$) and Instructions in Their Use. Biometrics, Sept. 1952.

Thompson, William R.: Use of Moving Averages and Interpolation to Estimate Median-Effective Dose. Bact. Rev., 1947.

Thompson, William R. and Weil, Carrol S.: On the Construction of Tables for Moving Average Interpolation. Biometrics, March 1952.

The $LD_{50}$ value for the present stabilizer is 2.48 g. per kilogram of weight, which is considerably higher than the values for other conventional organotin compounds employed as non-toxic stabilizers for vinyl chloride polymers.

A second feeding study was conducted for a period of 13 weeks using beagle dogs to determine the maximum concentration of the mono-n-octyltin mercaptoacetic acid esters of this invention which can be present in the food of these animals without causing any observable toxicological effect. This concentration level is referred to as the "no-effect level" by the United States Food and Drug Administration. A stabilizer of this invention mono-n-octyltin S,S',S''-tris(isooctylmercaptoacetate) was added to the food consumed by the dogs in amounts of 0, 100, 300 and 1,000 parts per million. The no-effect level was found to be 300 parts per million. This level of toxicity is considered to be unexpectedly low for an organotin compound.

The criteria employed to determine the absence of toxicological effects included general appearance, health, growth and food intake; blood analyses for enzyme activity and serum protein; kidney damage by urine analysis; change in weight of internal organs and presence of the tin compound in the kidneys, bones, brain, liver and blood.

EXAMPLE IV

This example demonstrates the efficacy of mono-n-octyltin-S,S',S''-tris(isooctylmercaptoacetate) as a stabilizer for vinyl chloride polymers.

The test samples employed in the following heat stability test were prepared using a mixture consisting of (1) 100 parts of a vinyl chloride homopolymer exhibiting an inherent viscosity of 0.84 as determined using ASTM test method no. 1243-60 (a) and available under the trade name Geon 110×223, (2) 18.5 parts of an acrylonitrilebutadiene-styrene terpolymer (Blendex 401), (3) 0.5 part of calcium stearate, (4) 0.5 parts of a low molecular weight polyethylene wax exhibiting a viscosity of 200 centipoises at 140° C. a softening point of 104° C. and an acid number of 15, (5) 0.1 part of Alizarin Irozol blue dye and (6) 2.0 parts mono-n-octyltin S,S',S''-tris(isooctylmercaptoacetate). The resultant mixture was blended for five minutes on a 2-roll differential speed mill wherein the roll temperature was 177° C. The continuous sheet which was formed during the milling operation as removed from the rolls and cut into squares measuring about 1 inch (2.54 cm.) along each side. The squares were rated as to color and placed in a circulating air oven heated to a temperature of 204° C. The samples were removed at 5 minute intervals and rated as to color. At this relatively high temperature the samples required between 20 and 25 minutes of heating to darken completely to a black color. By contrast, an unstabilized polymer composition turns black during the milling operation and adheres to the mill rolls.

The following color ratings were observed during the heat treatment.

Initial Color following milling—off white
After 5 minutes of heating—slight yellowness
After 10 minutes of heating—slight yellowness
After 15 minutes of heating—yellow
After 20 minutes of heating—yellow-brown
After 25 minutes of heating—black

What is claimed is:

[1. A food grade liquid organotin stabilizer for polyvinyl chloride and copolymers of vinyl chloride with copolymerizable ethylenically unsaturated compounds, wherein said stabilizer consists essentially of between 95 and 100% by weight of mono-n-octyltin compound of the general formula

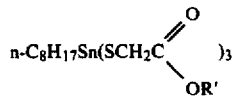

wherein R' represents an alkyl radical containing eight carbon atoms, the remaining 0–5% of said stabilizer consisting essentially of other octyltin compounds.]

[2. The food grade liquid organotin stabilizer of claim 1 wherein the mono-n-octyltin compound is mono-n-octyltin-S,S',S''-tris(isooctyl mercaptoacetate).]

[3. The food grade liquid organotin stabilizer of claim 2 which contains between 0 and 5%, based on the weight of the stabilizer of tri-n-octyltin-S-isooctyl mercaptoacetate.]

[4. The food grade liquid organotin stabilizer of claim 1 wherein said mono-n-octyltin compound is mono-n-octyltin-S,S',S''-tris(2-ethylhexyl mercaptoacetate).]

*5. A packaged foodstuff, comprising a food or beverage sealedly packaged within a shaped article packaging material which comprises a stabilized food grade vinyl halide polymer composition, said polymer composition comprising a nonhazardous effective stabilizing amount of a monoalkyltin compound having the formula n-*$C_8H_{17}Sn(SCH_2COOR)_3$ *wherein R is a linear or branched alkyl group of 8 carbon atoms and said compound being individually devoid of such contaminants and exhibiting such acute, chronic and no-effect toxicity levels and extractability values as to satisfy FDA Toxicity Quotient criteria.*

*6. The packaged foodstuff of claim 5, said vinyl halide polymer comprising a homopolymer or copolymer of vinyl chloride.*

*7. The packaged foodstuff of claim 6, said monoalkyltin compound having an acute oral toxicity of greater than 1 gram per kilogram of body weight, a maximum extraction from polyvinyl chloride by foodstuffs of less than 1 part per million, and a no-effect toxicity level for dogs of 300 parts per million per kilogram of foodstuff.*

*8. The packaged foodstuff of claim 7, said polymer composition further comprising an auxiliary food grade stabilizer.*

*9. The packaged foodstuff of claim 8, said polymer composition comprising a nonhazardous effective stabilizing amount of said monoalkyltin compound in admixture with di-n-octyltin-S,S'-bis(isooctylmercaptoacetate) auxiliary stabilizer.*

*10. The packaged foodstuff of claim 9, said admixture containing up to about 75% by weight of said auxiliary stabilizer.*

*11. The packaged foodstuff of claim 7, said polymer composition further comprising at least one antioxidant, plasticizer, impact modifying polymer, lubricant, ultra-violet absorber, dye, or mixture thereof.*

*12. The packaged foodstuff of claim 7 wherein said monoalkyltin compound is mono-n-octyltin-S,S',S''-tris-(isooctylmercaptoacetate).*

*13. The packaged foodstuff of claim 7 wherein said monoalkyltin compound is mono-n-octyltin-S,S',S''-tris(2-ethylhexylmercaptoacetate).*

*14. The packaged foodstuff of claim 7, said shaped article packaging material comprising a film.*

*15. The packaged foodstuff of claim 7, said shaped article packaging material comprising a bottle.*

*16. The packaged foodstuff of claim 7, said shaped article packaging material comprising a tray.*

*17. The packaged foodstuff of claim 7, said monoalkyltin compound having a purity of at least 95% by weight.*

*18. The packaged foodstuff of claim 7, said effective stabilizing amount ranging from 0.1 to 5% by weight.*

*19. The packaged foodstuff of claim 18, said effective stabilizing amount ranging from 1 to 2% by weight.*

*20. The packaged foodstuff of claim 9 wherein said monoalkyltin compound is mono-n-octyltin-S,S',S''-tris-(isooctylmercaptoacetate).*

*21. The packaged foodstuff of claim 9 wherein said monoalkyltin compound is mono-n-octyltin-S,S',S''-*tris(*2-ethylhexylmercaptoacetate).*

* * * * *